(12) United States Patent
Zaripov et al.

(10) Patent No.: US 10,386,349 B2
(45) Date of Patent: Aug. 20, 2019

(54) METHOD FOR DETECTING EXPLOSIVE DEVICES AND OTHER TARGET SUBSTANCES

(71) Applicant: PUBLIC JOINT STOCK COMPANY AEROFLOT-RUSSIAN AIRLINES, Moscow (RU)

(72) Inventors: Azat G. Zaripov, Moscow (RU); Klim T. Sulimov, Moscow (RU); Galina A. Kogun, Gorki (RU); Oleg A. Grigorev, Moscow (RU); Svetlana N. Lukyanova, Moscow (RU); Viktoriya A. Alekseeva, Khimki Moscow region (RU); Aleksandr E. Koklin, Moscow (RU)

(73) Assignee: AEROFLOT RUSSIAN AIRLINES PUBLIC JOINT STOCK COMPANY, Moscow (RU)

( * ) Notice: Subject to any disclaimer, the term of this patent is extended or adjusted under 35 U.S.C. 154(b) by 0 days.

(21) Appl. No.: 14/997,562

(22) PCT Filed: Mar. 23, 2015

(86) PCT No.: PCT/RU2015/000166
§ 371 (c)(1),
(2) Date: Jan. 17, 2016

(87) PCT Pub. No.: WO2015/174888
PCT Pub. Date: Nov. 19, 2015

(65) Prior Publication Data
US 2018/0031531 A1 Feb. 1, 2018

(30) Foreign Application Priority Data
May 13, 2014 (RU) .................. 2014119145

(51) Int. Cl.
*G01N 33/00* (2006.01)
*F41H 11/132* (2011.01)
*G01N 33/22* (2006.01)

(52) U.S. Cl.
CPC ....... *G01N 33/0001* (2013.01); *F41H 11/132* (2013.01); *G01N 33/227* (2013.01)

(58) Field of Classification Search
CPC . A61B 5/14552; A61B 5/6804; A61B 5/6831; F41H 11/132; G01N 33/0001; G01N 33/227
See application file for complete search history.

(56) References Cited

PUBLICATIONS

Züger M, Fritz T. Interruptibility of software developers and its prediction using psycho-physiological sensors. InProceedings of the 33rd Annual ACM Conference on Human Factors in Computing Systems Apr. 18, 2015 (pp. 2981-2990). ACM.*

(Continued)

*Primary Examiner* — Harshad R Patel
(74) *Attorney, Agent, or Firm* — Inventa Capital PLC

(57) ABSTRACT

A method for detecting explosives and other target substances using the detector canine is used to inspect the object by the detector canine accompanied by the handler who visually observes changes in the detector canine's behavior and determines the presence of explosives and/or other target substances when there are behavioral changes in the detector canine. With the changes in behavior of the detector canine during the inspection, the current complex psycho-physiological response of the detector canine is determined and compared with the previously determined response for odor detection. According to the response results, the conclusions regarding the detector canine detecting explosives and/or other target substances are made.

1 Claim, 2 Drawing Sheets

(56) References Cited

PUBLICATIONS

Lawson S, Kirman B, Linehan C, Feltwell T, Hopkins L. Problematising upstream technology through speculative design: the case of quantified cats and dogs. InProceedings of the 33rd Annual ACM Conference on Human Factors in Computing Systems Apr. 18, 2015 (pp. 2663-2672). ACM.*

Holliday, T. A., and Colette Williams. "Clinical Electroencephalography in Dogs (1999)." Clinical Electroencephalography 1.1 (1999).*

A. Bozkurt et al., "Toward Cyber-Enhanced Working Dogs for Search and Rescue," in IEEE Intelligent Systems, vol. 29, No. 6, pp. 32-39, Nov.-Dec. 2014.*

R. Brugarolas et al., "Behavior Recognition Based on Machine Learning Algorithms for a Wireless Canine Machine Interface", Proc. IEEE Body Sensor Networks Conf., pp. 1-5, 2013.*

Dorman DC, Sherman B, Gruen M, Fish R, Foster ML, Case B, Lazarowski L, Jeffries A. Developing the Second Generation of Improvised Explosive Device Detector Dog. North Carolina State Univ at Raleigh School of Veterinary Medicine; Apr. 15, 2013.*

Ahammed SS, Pillai BC. Design of Wi-Fi based mobile Electrocardiogram monitoring system on concerto platform. Procedia Engineering. Jan. 1, 2013;64:65-73.*

Sufi, Fahim, et al. "A mobile web grid based physiological signal monitoring system." Information Technology and Applications in Biomedicine, 2008. ITAB 2008. International Conference on. IEEE, 2008.*

Samson, Nathalie, et al. "Radio telemetry devices to monitor breathing in non-sedated animals." Respiratory physiology & neurobiology 179.2-3 (2011): 111-118.*

Polygraph. (2009). In A. S. Reber, R. Allen, & E. S. Reber, The Penguin dictionary of psychology (4th ed.). London, UK: Penguin. Retrieved from https://search.credoreference.com/content/entry/penguinpsyc/polygraph/0?institutionId=743.*

Hirano, Y., T. Oosawa, and K. Tonosaki. "Electroencephalographic olfactometry (EEGO) analysis of odour responses in dogs." Research in veterinary science69.3 (2000): 263-265.*

"Quantified Pet" Jul. 11, 2014. Accessed online at <www.scoop.it/t/quantified-pet?q-emotidog> on Apr. 4, 2018.*

* cited by examiner

METHOD FOR DETECTING EXPLOSIVE DEVICES AND OTHER TARGET SUBSTANCES

RELATED APPLICATIONS

This application claims priority to Patent Cooperation Treaty Application number PCT/RU2015/000166 filed on Mar. 23, 2015 and incorporated herewith by reference in its entirety.

FIELD OF THE INVENTION

The invention relates to methods for detecting explosives and other target substances using detector canines and can be used at airports, train stations, and other public places.

BACKGROUND OF THE INVENTION

Canines have an acute sense of smell which is their leading sensory organ. Because of their distinctly developed olfactory analyzer, detection sniffer dogs are used as olfactory detectors.

When specially trained detector canines detect the odor of the target substance, they give a signal to the handler by changing their behavior, in particular, by pose (the canine sits or lies near the detected source of the odor). The handler visually determines the change in the behavior of the detector canine, presumably corresponding to the odor detection of the target substances.

Patent US2009/0139459A1 «Canine certification method», IPC A01K29/00, G01N33/00, published on Jun. 4, 2009, describes the method for determining a particular canine's ability to detect target substances, including drugs and explosives, in which the handler and canine are placed in a sealed chamber and the odor is introduced into the chamber at predetermined concentration. Gradually the odor concentration in the chamber is increased and the animal is observed as to its reaction to the predetermined odor concentration. The method helps to select detector canines and to determine a predetermined threshold of sensitivity of the detector canine.

In the article "The Scent of Evil" by Olga Boguslayskaya, published in Moskovskij Komsomolets newspaper on Mar. 23, 2007, (the article can also be found on http://1001.ru/arc/mk/issue329/), the method for detecting explosives and other target substances is described. The method is based on visual observation of the behavior of detector canines, in which the control olfactory samples are placed in the room and the first canine is taken around the samples to determine the control sample with the odor of the target substance from the canine's behavior (the canine sits near the sample in which the odor of the target substance is concentrated). It is known that in order to receive a reward from the handler, the canine may give a false signal for detection of target substances. Since the detection accuracy of a target substance by one detector canine is not considered to be high enough, the first dog is removed from the room, the location of the control samples are changed, and the next canine is brought into the room and the experiment is repeated. Then the control samples are rearranged again and the canine is changed again. If all canines surely choose the same control sample, then the detection of the target substance is identified as positive.

The disadvantage of the method described in the article is the need for consistent use of multiple detector canines and handlers, which results in significant time and costs.

The prior art describes methods for determining psychophysiological state of humans based on the connection between occurring mental processes and the dynamics of physiological processes.

For example, Patent RU12970U1 "Device for aromatherapy," IPC7 A61L9/00, published on Mar. 20, 2000, describes the method for controlling psychophysiological state of humans when introducing the odor of a certain concentration, using an electroencephalograph, electrocardiograph, a device for measuring the frequency of heart beats, or polygraph. To receive information about changes in psychophysiological state of humans when inhaling the odor, the signals from the sensors installed on the person, for example, the sensor of heart rate or respiration frequency sensor, are transmitted to the input of the processing unit. In the processing unit, the information is processed, that is compared with data representing the "normal" state of a person.

The prior art describes methods for remote detection of explosives and other target substances using detector canines. See, for example, Patent RU2288488C1 "Device for detecting people under rubble and searching for explosives and drugs," IPC G01V11/00, published on Nov. 27, 2006, and Patent RU2426141C1 "Device for detecting people under rubble and searching for explosives and drugs," IPC G01S1/02, published on Aug. 10, 2011, in which the canine's heart rate is measured remotely and with sudden change of heart rate, it is decided that the detector canine detected explosives and other targeted substances.

The disadvantage of the above method is the low accuracy of the detection of explosives and other target substances, because changes in the pulse of the detector canine can be detected not only when detecting target substances, but also in other situations, such as when detecting a biological object.

Patent RU31718U1 "Device for measuring human psychophysiological parameters," IPC A61B 5/16, 5/02, 3/06, published on Aug. 27, 2003, describes the system for measuring human physiological parameters, including a computer and heart beat frequency sensors and respiratory frequency sensors connected to the computer inputs, electrocardiogram sensors (hereinafter referred to as ECG) and electroencephalogram sensors (hereinafter referred to as EEG). The system is designed for the simultaneous control of the nervous, respiratory, and cardiovascular systems in humans.

The closest prior art of the claimed invention is the method of detecting explosives and other targeted substances based on visual observation of the behavior of the detector canine in Patent US2012/0111285A1 "Dynamic canine tracking method for hazardous and illicit substances," IPC A01K15/00, published on May 10, 2012, in which detection of hazardous and other illicit substances is determined by the behavioral changes in detector canines.

The disadvantage of the method is low reliability in detecting target substances.

The task to be solved by this invention is a method for the detection of explosives and other target substances using detector canines. The method is characterized by high reliability and short inspection time.

SUMMARY OF THE INVENTION

The technical result which is the aim of the invention is to increase the detection reliability of explosives and other target substances using detector canines and to reduce the time required to conduct the inspection.

Said technical result is achieved by the method for detecting explosives and other target substances using detector canines, in which the site is inspected by the detector canine accompanied by the handler, detector canine's behavior is visually monitored for any changes, and when the detector canine's behavior changes, the presence of explosives and/or other target substances is determined.

Said technical result is achieved in that prior to the inspection of the object, a complex psychophysiological reaction of the detector canine is determined to detect the odor of explosives and/or other target substance of the predetermined concentration, and when the detector canine's behavior changes during the object inspection, the current complex psychophysiological reaction of the detector canine is determined and compared with its earlier response to the detection of a specific odor. By comparing the results, the conclusion is made about detector canine's detection of explosives and/or other target substances.

DETAILED DESCRIPTION OF THE INVENTION

Figure 1:
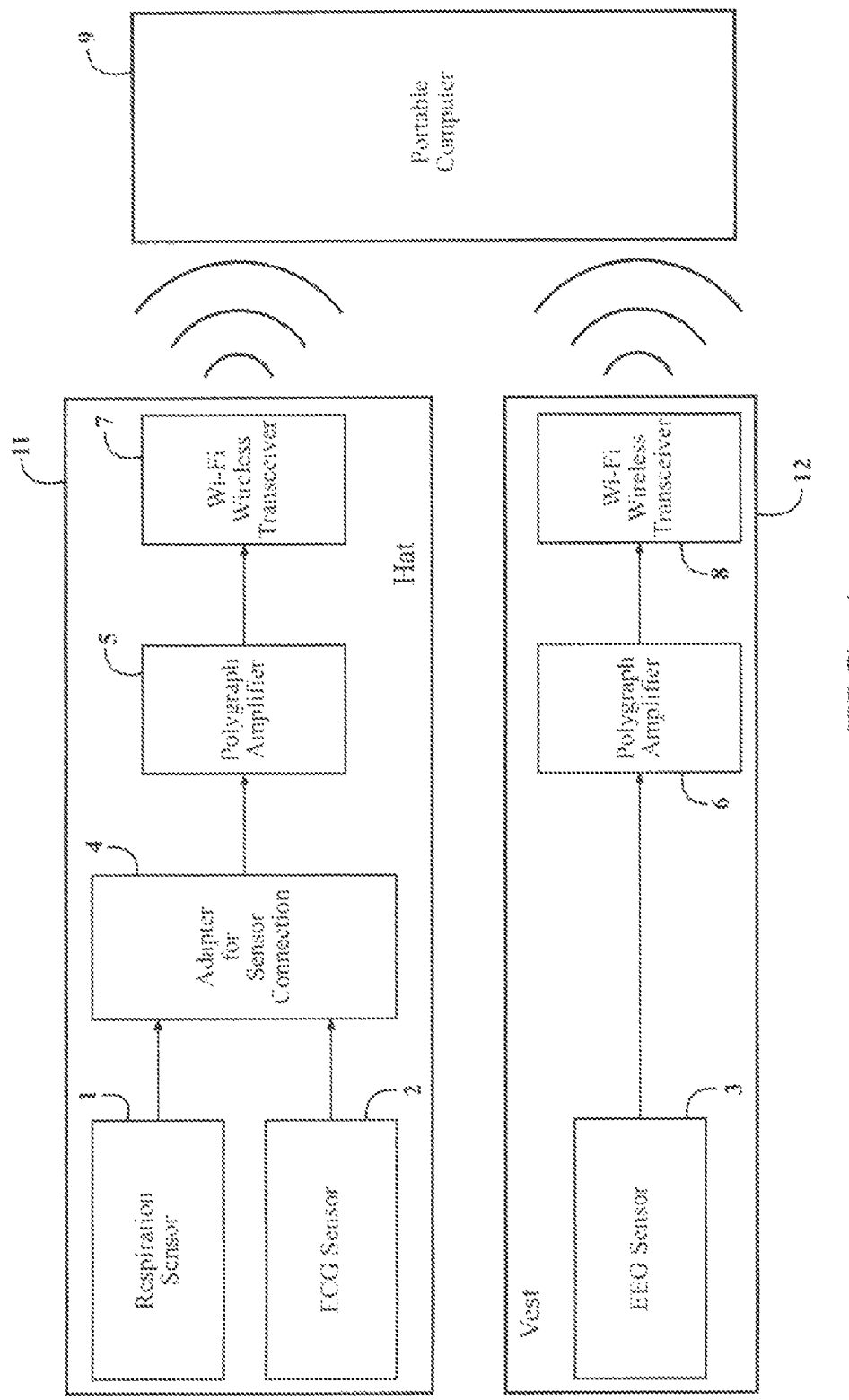
FIG. 1 illustrates the system for recording psychophysiological parameters of detector canine.
Figure 2:
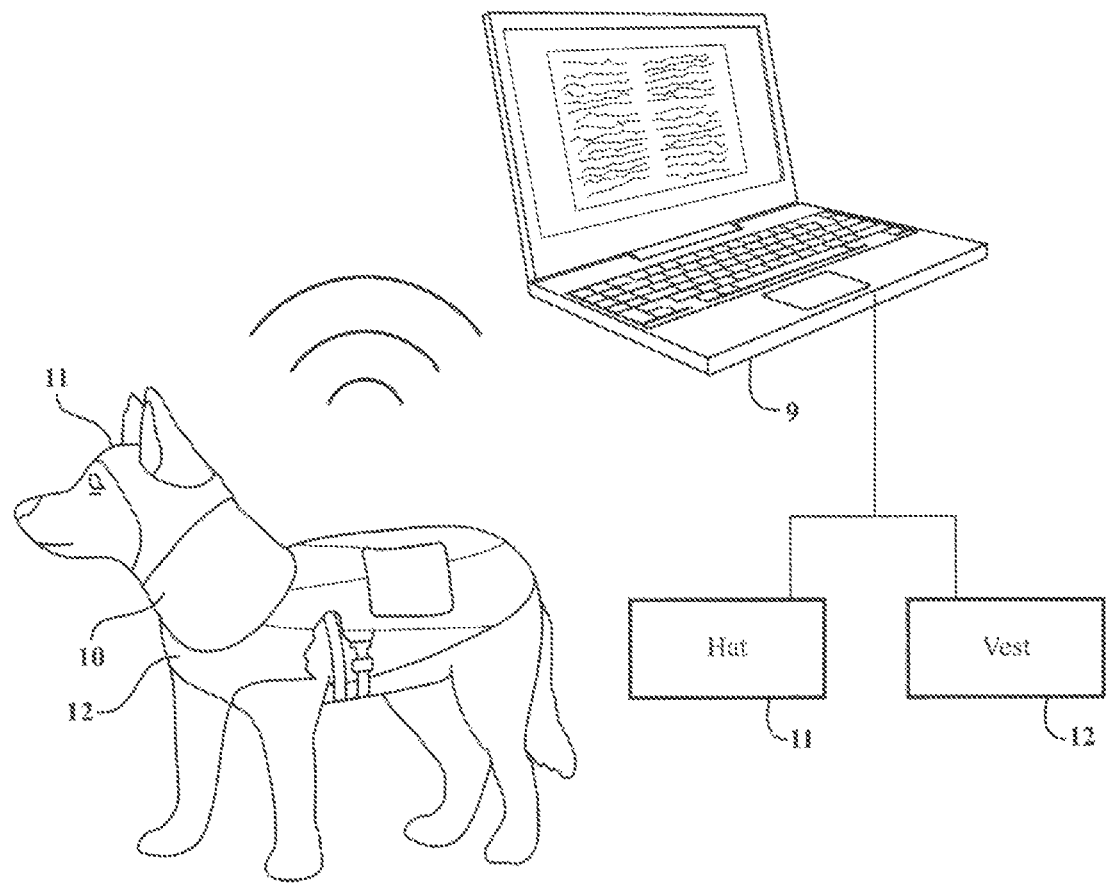
FIG. 2 illustrates the location of elements on the system.

Drawing positions are indicated as follows: 1 is a respiration sensor; 2 is ECG sensor; 3 is a EEG sensor; 4 is an adapter for sensor connection; 5, 6 is polygraph amplifier; 7, 8 is Wi-Fi wireless transceiver; 9 is a portable computer; 10 is a detector canine; 11 is a hat; and 12 is a vest. The method may be implemented using a system for recording psychophysiological parameters of detector canine shown in FIG. 1.

The system includes respiration sensor 1, ECG sensor 2, EEG sensor 3, adapter for sensor connection 4, polygraph amplifiers 5 and 6, Wi-Fi wireless transceivers 7 and 8, and portable computer 9 that should be able to connect to wireless Wi-Fi.

Active EEG sensors 3 are located on the detector canine's head 10 and are mounted on the hat 11. Passive respiration sensors 1 and ECG 2 are located on the detector canine's body and are mounted on vest 12. Adapter 4, polygraph amplifiers 5 and 6, and Wi-Fi wireless transceivers 7 and 8 are also mounted on vest 12. The embodiment for the method comprises the following steps. The following is done to prepare the detector canine. System elements 1-8 for recording psychophysiological parameters are mounted on the detector canine 10. A portable computer 9 (notebook, tablet, smartphone etc.) that should be able to connect to wireless Wi-Fi is placed near the detector canine 10 in the area with wireless Wi-Fi coverage. A complex psychophysiological response of the detection canine in a "normal" psychophysiological condition is recorded using the system for recording psychophysiological parameters. Odor concentration of explosives or other target substance is set up by the olfactometer (is not shown in FIGURES). The detector canine is taken past the odor sample of predetermined concentration. From the changes in the behavior of the detector canine (the canine sits), the decision of the detector canine is determined visually regarding the odor detection.

A complex psychophysiological response of the detector canine to detect the odor of predetermined concentration is determined and stored in the memory of the portable computer 9. When the object is inspected using the detector canine, the following steps are followed. System elements 1-8 for recording psychophysiological parameters are mounted on the detector canine 10. The handler is equipped with the portable computer 9. The detector canine 10 accompanied by the handler moves inside and outside the object that is being inspected.

From the changes in the behavior of the detector canine, the handler visually makes the decision regarding the odor detection of the explosive or other target substance by the detector canine. A current complex psychophysiological response of the detector canine 10 is recorded using the system for recording psychophysiological parameters and is stored in the memory of the portable computer 9. The current complex psychophysiological response of the detector canine 10 is compared with the previously determined response that is stored in the memory of the portable computer 9. According to the response results, the conclusions regarding the detector canine detecting explosives and/or other target substances are made. The use of the claimed invention confirmed its industrial applicability and complies with the claimed technical result. With this invention, the detection reliability of explosives and other target substances using detector canines is enhanced by confirming the detection using complex psychophysiological reaction of the detection canine. The inspection time is reduced and is achieved by confirmation of the detection of explosives and other target substances independent from the detector canine's behavior by the technical system for the recording psychophysiological parameters.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:
1. A method for detecting explosives and target substances using a detector canine, the method comprising:
mounting at least one active EEG sensor on a head of the detector canine;
mounting at least one passive respiration sensor, at least one ECG sensor, an adapter, plurality of polygraph amplifiers, and a plurality of wireless transceivers on a body of the detector canine;
wirelessly connecting a portable computing device to the plurality of wireless transceivers;
determining and recording a first complex psychophysiological response of the detector canine;
setting, via an olfactometer, a sample of an odor of an explosive or other target substance, wherein the sample has a predetermined odor concentration;
leading the detector canine past the sample;
visually determining a behavioral change of the detector canine based on the odor detected by the detector canine;
determining and recording a second complex psychophysiological response of the detector canine based on the odor detected by the detector canine;

inspecting, by the detector canine, an object having the odor of the explosive or the other target substance, wherein the detector canine is accompanied by a handler;
leading, by the handler, the detector canine inside and outside of the object;
visually determining, by the handler, a behavioral change of the detector canine based on the odor of the object detected by the detector canine;
determining and recording a third complex psychophysiological response of the detector canine based on the odor of the object detected by the detector canine after behavioral change of the detector canine based on the odor of the object is detected by the detector canine; and
comparing the third complex psychophysiological response with the first complex psychophysiological response and the second complex psychophysiological response of the detector canine.

\* \* \* \* \*